(12) United States Patent
Miao et al.

(10) Patent No.: US 9,398,855 B2
(45) Date of Patent: Jul. 26, 2016

(54) SYSTEM AND METHOD FOR MAGNETIC RESONANCE IMAGING BASED RESPIRATORY MOTION CORRECTION FOR PET/MRI

(71) Applicant: Siemens Aktiengesellschaft, Munich (DE)

(72) Inventors: Shun Miao, Lawrenceville, NJ (US); Rui Liao, West Windsor, NJ (US); Christophe Chefd'hotel, Jersey City, NJ (US)

(73) Assignee: Siemens Aktiengesellschaft, Munich (DE)

( * ) Notice: Subject to any disclaimer, the term of this patent is extended or adjusted under 35 U.S.C. 154(b) by 158 days.

(21) Appl. No.: 14/291,568

(22) Filed: May 30, 2014

(65) Prior Publication Data

US 2014/0355855 A1 Dec. 4, 2014

Related U.S. Application Data

(60) Provisional application No. 61/828,976, filed on May 30, 2013.

(51) Int. Cl.
| | |
|---|---|
| A61B 5/00 | (2006.01) |
| A61B 5/055 | (2006.01) |
| A61B 6/00 | (2006.01) |
| A61B 6/03 | (2006.01) |
| G06T 7/00 | (2006.01) |
| G01R 33/48 | (2006.01) |
| G01R 33/565 | (2006.01) |

(52) U.S. Cl.
CPC .............. *A61B 5/0035* (2013.01); *A61B 5/055* (2013.01); *A61B 5/721* (2013.01); *A61B 6/037* (2013.01); *A61B 6/5205* (2013.01); *A61B 6/5264* (2013.01); *G01R 33/481* (2013.01); *G01R 33/56509* (2013.01); *G06T 7/0024* (2013.01); *A61B 6/4417* (2013.01); *A61B 6/5247* (2013.01); *G06T 2207/10016* (2013.01); *G06T 2207/10088* (2013.01); *G06T 2207/10104* (2013.01)

(58) Field of Classification Search
None
See application file for complete search history.

(56) References Cited

U.S. PATENT DOCUMENTS

| | | | |
|---|---|---|---|
| 4,905,699 | A | 3/1990 | Sano et al. |
| 6,292,684 | B1 | 9/2001 | Du et al. |
| 6,894,494 | B2 | 5/2005 | Stergiopoulos et al. |
| 7,561,909 | B1 | 7/2009 | Pai et al. |

(Continued)

OTHER PUBLICATIONS

J. Ouyang, et al. "Magnetic Resonance-Based Motion Correction for Positron Emission Tomography Imaging," Semin Nucl Med, vol. 43, No. 1, Jan. 2013, pp. 60-67, available online: Nov. 22, 2012.*

(Continued)

*Primary Examiner* — Matthew Bella
*Assistant Examiner* — Soo Shin

(57) ABSTRACT

A method and system for magnetic resonance imaging (MRI) based motion correction in position emission tomography (PET) images is disclosed. A static 3D magnetic resonance (MR) image of a patient is received. PET image data of the patient and a series of 2D MR images of the patient acquired simultaneous to the acquisition of the PET image data are received. A 3D+t motion field is estimated by registering the series of 2D MR images acquired at the plurality of time points to the static 3D MR image. A motion corrected PET image is generated based on the estimated 3D+t motion field using motion corrected PET reconstruction.

20 Claims, 3 Drawing Sheets

(56) References Cited

U.S. PATENT DOCUMENTS

| | | | |
|---|---|---|---|
| 7,689,019 B2* | 3/2010 | Boese | G03B 42/023 |
| | | | 128/922 |
| 7,729,467 B2 | 6/2010 | Kohlmyer et al. | |
| 8,411,915 B2* | 4/2013 | Wischmann | A61B 6/503 |
| | | | 382/128 |
| 8,417,007 B2 | 4/2013 | Yui | |
| 8,427,153 B2 | 4/2013 | Hu et al. | |
| 8,575,933 B2 | 11/2013 | Hu et al. | |
| 8,768,034 B2 | 7/2014 | Liu et al. | |
| 8,824,757 B2 | 9/2014 | Kolthammer et al. | |
| 2005/0113667 A1* | 5/2005 | Schlyer | A61B 6/037 |
| | | | 600/411 |
| 2005/0123183 A1 | 6/2005 | Schleyer et al. | |
| 2007/0088212 A1 | 4/2007 | Takei et al. | |
| 2007/0249911 A1* | 10/2007 | Simon | G06Q 50/24 |
| | | | 600/300 |
| 2008/0175455 A1* | 7/2008 | John | A61B 6/032 |
| | | | 382/130 |
| 2008/0246776 A1* | 10/2008 | Meetz | G06T 3/4007 |
| | | | 345/634 |
| 2008/0273780 A1 | 11/2008 | Kohlmyer et al. | |
| 2009/0037130 A1* | 2/2009 | Feiweier | A61B 6/032 |
| | | | 702/104 |
| 2010/0329528 A1* | 12/2010 | Hajnal | A61B 5/055 |
| | | | 382/131 |
| 2011/0044524 A1* | 2/2011 | Wang | G01R 33/54 |
| | | | 382/131 |
| 2013/0197347 A1 | 8/2013 | Moghari et al. | |
| 2013/0303898 A1 | 11/2013 | Kinahan et al. | |

OTHER PUBLICATIONS

M. von Siebenthal, et al. "4D MR imaging of respiratory organ motion and its variability," Phys. Med. Biol, vol. 52, Feb. 16, 2007, pp. 1547-1564.*

L. Gattinoni, et al. "What has computed tomography taught us about the acute respiratory distress syndrome?" Am J Respir Crit Care Med. Nov. 1, 2001;164(9):1701-11.*

J Ouyang, et al., "Magnetic Resonance-Based Motion Correction for Positron Emission Tomography Imaging," Seminars in Nuclear Medicine, vol. 43, No. 1, Jan. 2013, pp. 60-67, available online: Nov. 22, 2012.*

AD Copeland, et al., "Spatio-Temporal Data Fusion for 3D+T Image Reconstruction in Cerebral Angiography," IEEE Transactions on Medical Imaging, vol. 29, No. 6, Jun. 2010. pp. 1238-1251.*

JD Green, et al., "Comparison of X-Ray Fluoroscopy and Interventional Magnetic Resonance Imaging for the Assessment of Coronary Artery Stenoses in Swine," Magnetic Resonance in Medicine, vol. 54, pp. 1094-1099, 2005.*

* cited by examiner

SYSTEM AND METHOD FOR MAGNETIC RESONANCE IMAGING BASED RESPIRATORY MOTION CORRECTION FOR PET/MRI

This application claims the benefit of U.S. Provisional Application No. 61/828,976, filed May 30, 2013, the disclosure of which is herein incorporated by reference.

BACKGROUND OF THE INVENTION

The present invention relates to motion correction in medical image data, and more particularly to magnetic resonance imaging (MRI) based respiratory motion correction for PET/MRI image data.

Modern positron emission tomography (PET) imaging techniques have led to widespread use of PET, including in oncology, neuroimaging, cardiology, and pharmacology. However, PET image data often suffers from image degradation due to patient motion during the PET image data acquisition. Motion can occur due to normal breathing, heartbeat, and gross patient movement during the image acquisition. Among the different types of motion, respiratory motion typically has the largest impact on thoracic and abdomen imaging due to its large magnitude and the larger variation of breathing patterns.

Various techniques have been used to minimize the effects of respiratory motion in image acquisition, including breath holding, respiratory gating, and advanced reconstruction techniques. Due to the long acquisition time of PET (typically one to three minutes per bed position), breath holding techniques are difficult to apply. Respiratory gating strategies divide a breathing cycle into several phases, which can be measured by a navigation signal (e.g., using a respiratory belt). List-mode PET data are then clustered into different breathing phases based on the navigation signal to "freeze" to motion. However, such respiratory gating techniques assume that respiratory motions in the same breathing phase are identical across different breathing cycles, which is not true due to the fact that breathing motion patterns can be irregular, especially when the patient is under stress, anxiety, and/or pain.

PET/MRI image acquisition systems allow for simultaneous acquisition of PET and MR data with accurate alignment in both temporal and spatial domains. However, 4D MR image data with a high spatial resolution typically has a very low temporal resolution, which limits its usefulness for motion estimation. Recently, some techniques have been proposed to take advantage of simultaneous PET/MRI acquisition for PET respiratory and cardiac motion correction. However, due to the tradeoff between spatial and temporal resolution of MR imaging, all of the proposed methods rely on gating for 3D MRI acquisition. Accordingly, these methods suffer from the same drawbacks as other respiratory gating techniques.

BRIEF SUMMARY OF THE INVENTION

The present invention provides a method and system for MRI based motion correction in a PET image. Embodiments of the present invention can be used for motion correction of a PET image acquired in a PET/MRI image acquisition system. Embodiments of the present invention acquire a series of dynamic 2D MR images during the PET image data acquisition, and register the 2D MR images against a static 3D MRI to estimate a motion field. The motion field can then be used in PET image reconstruction for motion correction of the PET image data.

In one embodiment of the present invention, a static 3D magnetic resonance (MR) image of a patient is received. PET image data of the patient is received. A series of 2D MR images of the patient acquired at a plurality of time points simultaneous to acquisition of the PET image data is received. A 3D+t motion field is estimated by registering the series of 2D MR images acquired at the plurality of time points to the static 3D MR image. A motion corrected PET image is generated based on the estimated 3D+t motion field using motion corrected PET reconstruction.

These and other advantages of the invention will be apparent to those of ordinary skill in the art by reference to the following detailed description and the accompanying drawings.

DETAILED DESCRIPTION

The present invention provides a method and system for MRI based motion correction in a PET image. Embodiments of the present invention are described herein to give a visual understanding of the motion correction method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a method of PET motion correction that utilizes a series of 2D MR images with a respiratory motion model for respiratory motion estimation. The use of 2D MR images for motion estimation instead of 3D MR images is advantageous due to the fact that 2D MRI acquisition can achieve a higher temporal resolution and thus does not require gating. According to an embodiment of the present invention, a series of dynamic 2D MR images are acquired during PET data acquisition, and the 2D MR images are registered against a static 3D MR image to estimate a motion field. The motion field can then be applied in the PET image reconstruction for motion correction.

Figure 1:
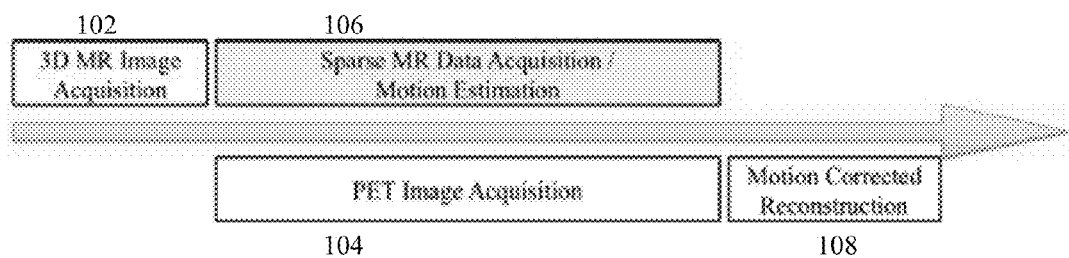
FIG. 1 illustrates a workflow for a motion corrected PET/MRI imaging method according to an embodiment of the present invention.

FIG. 1 illustrates a workflow for a motion corrected PET/MRI imaging method according to an embodiment of the present invention. As illustrated in FIG. 1, 3D MR image acquisition (102) is performed to acquire a 3D MR image which provides a detailed anatomy of a patient. Following the 3D MR image acquisition, PET image acquisition (104) and sparse MR data acquisition and Motion estimation (106) are performed simultaneously. In particular, following the 3D MR image acquisition, the acquisition of the PET image data is started and 2D MR images are acquired simultaneously throughout the whole PET image data acquisition process resulting in a series of dynamic 2D MR images. With the series of dynamic 2D MR images and the static 3D MR image, a 3D+t (three-dimensional plus time) motion filed is estimated and used for correcting patient motion in the motion corrected PET image reconstruction (108). The workflow of FIG. 1 is described in greater detail in the description of FIG. 2 below.

Figure 2:
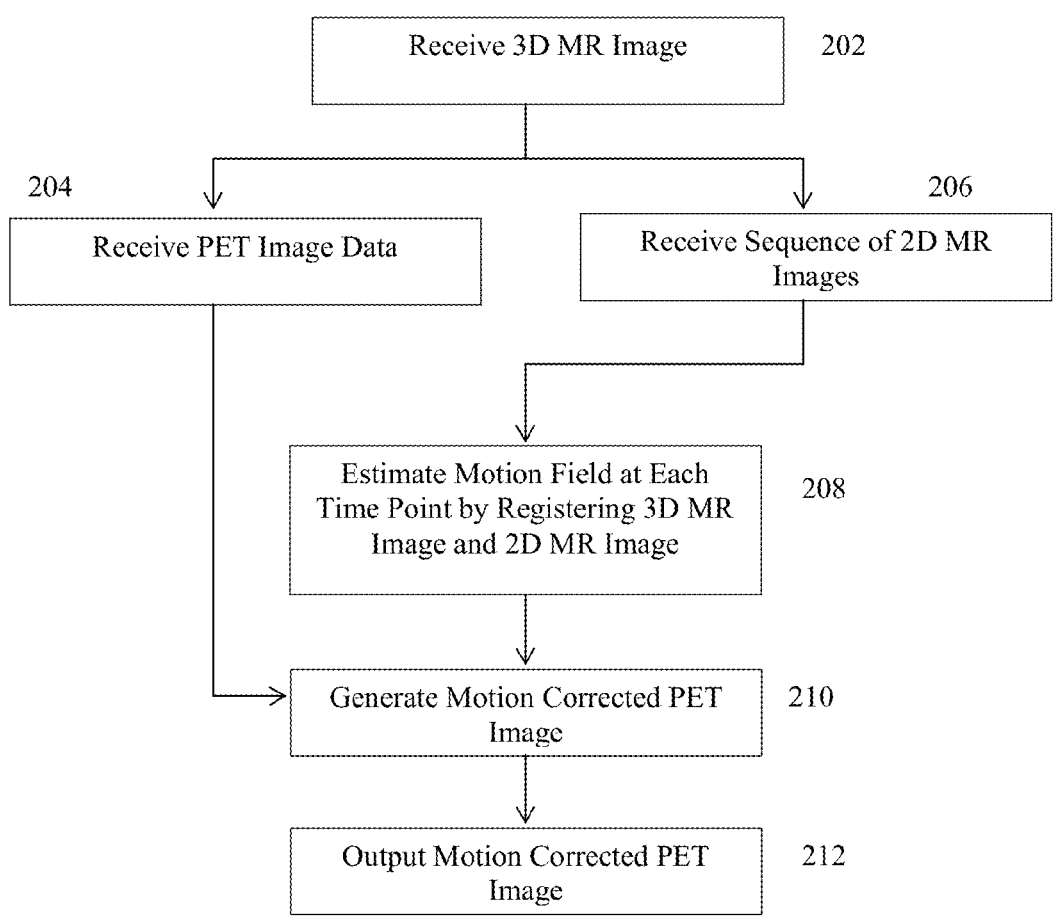
FIG. 2 illustrates a method for MRI based motion correction of a PET image according to an embodiment of the present invention.

FIG. 2 illustrates a method for MRI based motion correction of a PET image according to an embodiment of the present invention. The method of FIG. 2 transforms image data representing anatomy of patient to generate a motion corrected PET image of a patient. At step 202, a 3D MR image of a patient is received. The 3D MR image may be acquired using an MR scanner. In an advantageous implementation, the 3D MR image may be acquired using an MR scanner of a combined PET/MRI image acquisition device. The 3D MR image may be received directly from the MR scanner or the 3D MR image may be received by loading a previously stored 3D MR image. In an advantageous embodiment, the 3D MR image is acquired prior to acquiring PET image data of the patient. However, the present invention is not limited thereto. For example, in an alternative embodiment, the 3D MR image may be acquired subsequent to the acquisition of the PET image data.

At step 204, PET image data of the patient is received. The PET image data is acquired using a PET scanner. In an advantageous implementation, the PET data is acquired using a PET scanner of a combined MRI/PET image acquisition device. The PET image data may be received directly from the PET scanner or the PET image data may be received by loading previously stored PET image data.

At step 206, a series of 2D MR images is received. The 2D MR images are acquired simultaneously to PET image acquisition. In particular, during the PET image acquisition, a 2D MR image is acquired at each of a plurality of time points, resulting in the series of 2D MR images. For example, a 2D MR image can be acquired at 100 ms intervals throughout the PET image acquisition. The 2D MR images can be acquired at different locations and/or orientations at different time points to capture as much information of patient motion as possible. For example, the 2D MR images can be slices in the transverse plane acquired by sweeping back and forth along the head-foot direction of the patient. It is to be understood that a variety of possible locations and orientations are possible for the 2D MRI acquisition and the present invention is not limited to any particular scan plan for acquiring the 2D MR images. The 2D MR images are acquired using an MR scanner. In an advantageous implementation, the 2D MR images are acquired using an MR scanner of a combined PET/MRI image acquisition device simultaneously to the PET image data being acquired using the combined PET/MRI image acquisition device. The 2D MR images may be received directly from the MR scanner or the 2D MR images may be received by loading a stored series of 2D MR images.

At step 208, a motion field is estimated at each time point at which a 2D MRI image was acquired by registering the 3D MR image and each 2D MR image. Given the static 3D MR image and the series of dynamic 2D MR images, a 3D+t motion field is estimated at each time point $t_i$ at which a 2D MR image is acquired. However, a single 2D MR image only provides sparse information of the 3D motion field and therefore it would be difficult to use a single 2D MR image alone to estimate an accurate 3D motion field. Due to the fact that 2D MR images can be acquired at a much higher rate than respiratory motion, the 3D+t motion field has a strong correlation between neighboring frames and therefore can be jointly estimated from a series of sparse 2D MR images. Thus, according to an advantageous embodiment of the present invention, the motion estimation is formulated as a registration problem between a static 3D MR image and a series of dynamic 2D MR images.

The static 3D MR image is denoted as $V(x^{3d})$ and the dynamic 2D MR image sequence is denoted as $I(x^{2d}, t_i)$, where $x^{3d}$ and $x^{2d}$ are 3D and 2D coordinates, respectively. The location of the 2D MR slice at $t_i$ is represented by a mapping $D(t_i): \mathbb{R}^2 \to \mathbb{R}^3$, which maps 2D coordinates in the 2D MR image to the 3D space of the 3D MR image. The 3D+t motion field is denoted as $u(x^{3d}, t_i)$, which indicates each voxels' displacement with respect to the reference image V at time $t_i$. For ease of presentation, $U(V, t_i)$ is used to denote the volume transformed by $u(x^{3d}, t_i)$:

$$U(V, t_i)(x^{3d}) = V(x^{3d} - u(x^{3d}, t_i)).$$

The 3D+t motion field is estimated by minimizing and energy function:

$$E(u(x^{3d}, t_i)) = E_{image}(u(x^{3d}, t_i)) + \lambda \cdot E_{model}(u(x^{3d}, t_i)),$$

where $E_{image}$ and $E_{model}$ are image and model energy terms, respectively, and $\lambda$ is a weight of the model energy. The minimization of the energy function searches for the motion field at each time step that achieves the best combination of a transformed volume resulting that matches the respective 2D MR image at that time step and the motion field matching a predicted motion field based on a respiratory model. According to a possible implementation, once the 3D+t motion field is calculated for each time step, the 3D+t motion field may be interpolated to generate a continuous 3D+t motion field over the time period of the PET image acquisition.

The image energy $E_{image}$ compares the transformed volume and the 2D MR image at each time step. In an advantageous implementation, the image energy $E_{image}$ can be defined as a negative intensity-based similarity measure between the 2D MR image $I(x^{2d}, t_i)$ and the corresponding slice extracted from the transformed volume $U(V, t_i)$:

$$E_{image}(u(x^{3d}, t_i)) = -\Sigma_i \delta(U(V, t_i), I(x^{2d}, t_i)),$$

where $\delta(\cdot, \cdot)$ is an intensity based similarity measure. For example, choices for $\delta(\cdot, \cdot)$ include, but are not limited to, Mutual Information, Cross Correlation, and Pattern Intensity measures.

The model energy $E_{model}$ compares the motion filed field to a predicted motion field using a respiratory model. In an advantageous implementation, the model energy $E_{model}$ is the dissimilarity between the 3D+t motion field $u(x^{3d}, t_i)$ and a respiratory motion model $u_0(x^{3d}, p)$, where $p \in [0,1)$ is the phase of breathing. The respiratory motion model describes a typical motion pattern for different phases of breathing. The respiratory model provides an additional constraint to improve accuracy of the motion field calculation using the sparse 2D MR images. A navigation signal, such as a respiratory belt, is used to detect a breath phase $p(t_i)$ corresponding to each time point $t_i$, and the model energy can be calculated as:

$$E_{model}(u(x^{3d}, t_i)) = \Sigma_i \mathcal{D}(u(x^{3d}, t_i), u_0(x^{3d}, p(t_i))),$$

where $D(\cdot, \cdot)$ measures the difference between the two deformation fields.

The target of the respiratory motion model is to describe a typical breathing pattern for a human. Mathematically, the respiratory motion model is described as a 3D+p motion field with respect to a 3D MRI atlas, denoted as $\hat{u}(x^{3d}, p)$, where p is a breathing phase. The standard motion model $\hat{u}(x^{3d}, p)$ can be generated by statistical modeling, biomechanical modeling, or elastic modeling. The embodiment described herein focuses on statistical modeling for explanation purposes, but the present invention is not limited to any specific modeling technique.

A statistical model for the respiratory model is trained from a group of training data, which is typically 3D+t MR or CT data of the chest and/or abdomen, covering at least one breathing cycle in the time domain. Dynamic motion fields are then extracted from the training data using image registration techniques. The extracted 3D+t motion fields are subject-specific to the training data, denoted as $u_k(x^{3d},p)$. To generate a standard (or average) motion model, a reference frame is selected for a certain breathing phase (e.g., max inhale) from each training data and each reference frame is registered to an atlas to generate a respective warping function $\phi_k$. The subject-specific model fields are then warped to the atlas and averaged to generate a standard motion model:

$$\hat{u}(x^{3d}, p) = \frac{1}{N}\sum_{k=1}^{N} \phi_k \cdot u_k(x^{3d}, p).$$

To apply the model to a patient, the 3D MR image of the patient is registered to the atlas to obtain a warping function $\phi_0$. The inverse of the warping function is then applied on the standard model $\hat{u}(x^{3d},p)$ to generate a subject-specific motion model:

$$u_0(x^{3d},t_i) = \phi_0^{-1} \cdot \hat{u}(x^{3d},p).$$

If the image acquisition time is not critical, the subject-specific motion model $u_0(x^{3d},t_i)$ can also be obtained by performing a gated 3D+t MR scanning before the PET data acquisition to reconstruct a whole breathing cycle. The 3D MR images at different breathing phases can then be registered to a reference frame to obtain a subject-specific motion model for the patient.

Returning to FIG. 2, at step 210, a motion corrected PET image is generated. Once the 3D+t motion field is estimated, the motion field can be incorporated into the list-mode PET image data for motion-corrected PET image reconstruction. For example, the maximum-likelihood expectation-maximization PET reconstruction algorithm can incorporate the motion field and reconstruct all detected coincidences in a single image while modeling the effect of motion emission and the attenuation maps. The motion-corrected PET image reconstruction results in a motion corrected PET image.

At step 212, the motion corrected PET image is output. For example, the motion corrected PET image can be output by displaying the motion corrected PET image on a display device of a computer system. The motion corrected PET image can be displayed alone or together with the 3D and/or 2D MR images. The motion corrected PET image can also be combined with the 3D or 2D MR images resulting in a PET/MRI fusion image, which can be displayed on a display device of a computer system. The motion corrected PET image can also be output by storing the motion corrected PET image on a memory or storage of a computer system.

Figure 3:
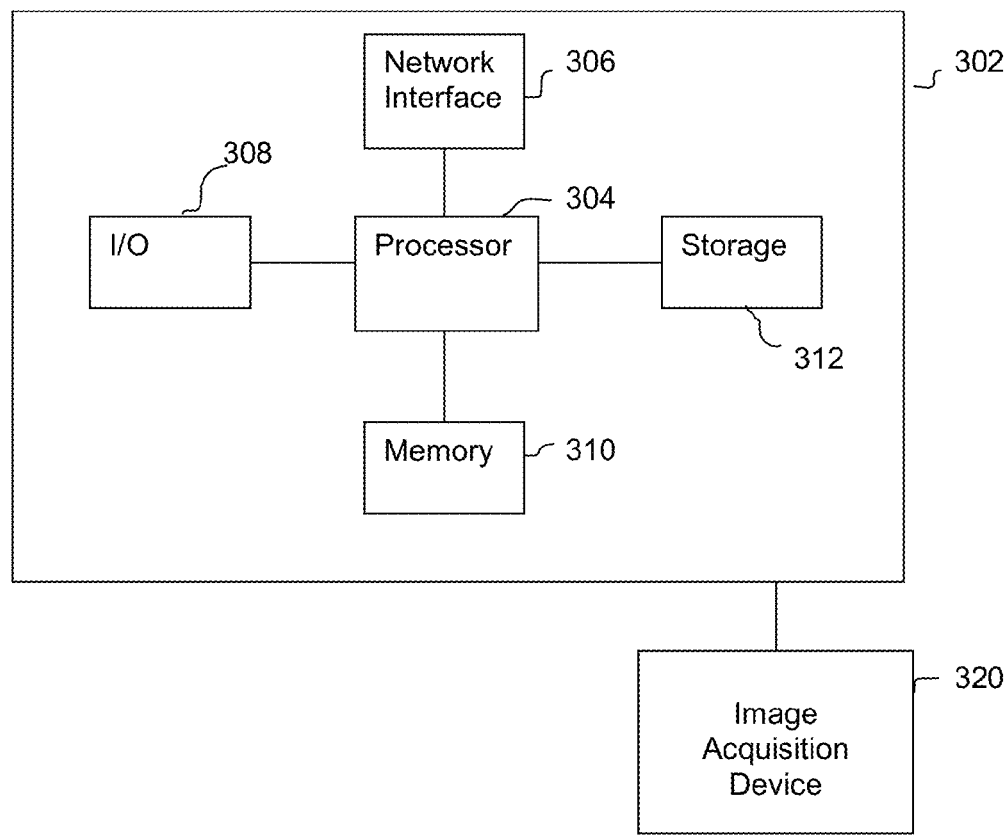
FIG. 3 is a high-level block diagram of a computer capable of implementing the present invention.

The above-described methods for MRI-based motion correction for PET images can be implemented on a computer using well-known computer processors, memory units, storage devices, computer software, and other components. A high-level block diagram of such a computer is illustrated in FIG. 3. Computer 302 contains a processor 304, which controls the overall operation of the computer 302 by executing computer program instructions which define such operation. The computer program instructions may be stored in a storage device 312 (e.g., magnetic disk) and loaded into memory 310 when execution of the computer program instructions is desired. Thus, the steps of the methods of FIGS. 1 and 2 may be defined by the computer program instructions stored in the memory 310 and/or storage 312 and controlled by the processor 304 executing the computer program instructions. An image acquisition device 320, such as a PET/MRI image acquisition device, etc., can be connected to the computer 302 to input image data to the computer 302. It is possible to implement the image acquisition device 320 and the computer 302 as one device. It is also possible that the image acquisition device 320 and the computer 302 communicate wirelessly through a network. The computer 302 also includes one or more network interfaces 306 for communicating with other devices via a network. The computer 302 also includes other input/output devices 308 that enable user interaction with the computer 302 (e.g., display, keyboard, mouse, speakers, buttons, etc.). One skilled in the art will recognize that an implementation of an actual computer could contain other components as well, and that FIG. 3 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for magnetic resonance imaging (MRI) based motion correction in position emission tomography (PET) images, comprising:
   receiving a static 3D magnetic resonance (MR) image of a patient;
   receiving PET image data of the patient;
   receiving a series of 2D MR images of the patient acquired at a plurality of time points simultaneous to acquisition of the PET image data;
   estimating a 3D+t motion field by registering the series of 2D MR images acquired at the plurality of time points to the static 3D MR image, wherein estimating a 3D+t motion field by registering the series of 2D MR images acquired at the plurality of time points to the static 3D MR image comprises:
   estimating the 3D+t motion field using the registration of the series of 2D MR images and the static 3D MR image and a predictive respiratory motion model; and
   generating a motion corrected PET image based on the estimated 3D+t motion field using motion corrected PET reconstruction.

2. The method of claim 1, wherein estimating a 3D+t motion field by registering the series of 2D MR images acquired at the plurality of time points to the static 3D MR image comprises:
   estimating a 3D+t motion field that minimizes an energy function including an image energy term and a model energy term.

3. The method of claim 2, wherein the image energy term compares each 2D MR image to a corresponding slice of a transformed volume resulting from transforming the static 3D volume based on the 3D+t motion field at the respective one of the plurality of time points, and the model energy term compares the 3D+t motion field and a predicted motion field calculated using the predictive respiratory motion model.

4. The method of claim 3, wherein the image energy term is a negative intensity-based similarity measure between each 2D MR image and the corresponding slice of the transformed volume.

5. The method of claim 3, wherein the model energy term measures a difference between the 3D+t motion field at each of the plurality of time steps and the predictive respiratory motion model at a breathing phase corresponding to each of the plurality of time steps.

6. The method of claim 5, wherein the breathing phase corresponding to each of the plurality of time steps is detected using a navigation signal.

7. The method of claim 3, further comprising:
registering the static 3D image to an atlas used to train a standard respiratory motion model to obtain a warping function; and
applying an inverse of the warping function to the standard respiratory motion model to obtain a patient-specific respiratory motion model, wherein the model energy term compares the 3D+t motion field and the patient-specific respiratory motion model.

8. The method of claim 1 wherein the series of 2D MR images are slices in the transverse plane acquired in a sweep along a head-foot direction of the patient.

9. An apparatus for magnetic resonance imaging (MRI) based motion correction in position emission tomography (PET) images, comprising:
a processor; and
a memory storing computer program instructions, which when executed on the processor, cause the processor to perform operations comprising:
receiving a static 3D magnetic resonance (MR) image of a patient;
receiving PET image data of the patient;
receiving a series of 2D MR images of the patient acquired at a plurality of time points simultaneous to acquisition of the PET image data;
estimating a 3D+t motion field by registering the series of 2D MR images acquired at the plurality of time points to the static 3D MR image, wherein estimating a 3D+t motion field by registering the series of 2D MR images acquired at the plurality of time points to the static 3D MR image comprises:
estimating the 3D+t motion field using the registration of the series of 2D MR images and the static 3D MR image and a predictive respiratory motion model; and
generating a motion corrected PET image based on the estimated 3D+t motion field using motion corrected PET reconstruction.

10. The apparatus of claim 9, wherein estimating a 3D+t motion field by registering the series of 2D MR images acquired at the plurality of time points to the static 3D MR image comprises:
estimating a 3D+t motion field that minimizes an energy function including an image energy term and a model energy term.

11. The apparatus of claim 10, wherein the image energy term compares each 2D MR image to a corresponding slice of a transformed volume resulting from transforming the static 3D volume based on the 3D+t motion field at the respective one of the plurality of time points, and the model energy term compares the 3D+t motion field and a predicted motion field calculated using the predictive respiratory motion model.

12. The apparatus of claim 11, wherein the image energy term is a negative intensity-based similarity measure between each 2D MR image and the corresponding slice of the transformed volume.

13. The apparatus of claim 11, wherein the model energy term measures a difference between the 3D+t motion field at each of the plurality of time steps and the predictive respiratory motion model at a breathing phase corresponding to each of the plurality of time steps.

14. The apparatus of claim 11, the operations further comprising:
registering the static 3D image to an atlas used to train a standard respiratory motion model to obtain a warping function; and
applying an inverse of the warping function to the standard respiratory motion model to obtain a patient-specific respiratory motion model, wherein the model energy term compares the 3D+t motion field and the patient-specific respiratory motion model.

15. A non-transitory computer readable medium storing computer program instructions for magnetic resonance imaging (MRI) based motion correction in position emission tomography (PET) images, the computer program instructions when executed on a processor cause the processor to perform operations comprising:
receiving a static 3D magnetic resonance (MR) image of a patient;
receiving PET image data of the patient;
receiving a series of 2D MR images of the patient acquired at a plurality of time points simultaneous to acquisition of the PET image data;
estimating a 3D+t motion field by registering the series of 2D MR images acquired at the plurality of time points to the static 3D MR image, wherein estimating a 3D+t motion field by registering the series of 2D MR images acquired at the plurality of time points to the static 3D MR image comprises:
estimating the 3D+t motion field using the registration of the series of 2D MR images and the static 3D MR image and a predictive respiratory motion model; and
generating a motion corrected PET image based on the estimated 3D+t motion field using motion corrected PET reconstruction.

16. The non-transitory computer readable medium of claim 15, wherein estimating a 3D+t motion field by registering the series of 2D MR images acquired at the plurality of time points to the static 3D MR image comprises:
estimating a 3D+t motion field that minimizes an energy function including an image energy term and a model energy term.

17. The non-transitory computer readable medium of claim 16, wherein the image energy term compares each 2D MR image to a corresponding slice of a transformed volume resulting from transforming the static 3D volume based on the 3D+t motion field at the respective one of the plurality of time points, and the model energy term compares the 3D+t motion field and a predicted motion field calculated using the predictive respiratory motion model.

18. The non-transitory computer readable medium of claim 17, wherein the image energy term is a negative intensity-based similarity measure between each 2D MR image and the corresponding slice of the transformed volume.

19. The non-transitory computer readable medium of claim 17, wherein the model energy term measures a difference between the 3D+t motion field at each of the plurality of time steps and the predictive respiratory motion model at a breathing phase corresponding to each of the plurality of time steps.

20. The non-transitory computer readable medium of claim 17, the operations further comprising:
- registering the static 3D image to an atlas used to train a standard respiratory motion model to obtain a warping function; and
- applying an inverse of the warping function to the standard respiratory motion model to obtain a patient-specific respiratory motion model, wherein the model energy term compares the 3D+t motion field and the patient-specific respiratory motion model.

* * * * *